United States Patent [19]

Hromatka et al.

[11] 4,230,873
[45] Oct. 28, 1980

[54] THIOPHENE DERIVATIVES

[75] Inventors: Otto Hromatka; Dieter Binder, both of Vienna, Austria

[73] Assignee: Hoffmann-La Roche Inc., Nutley, N.J.

[21] Appl. No.: 773,716

[22] Filed: Mar. 2, 1977

Related U.S. Application Data

[63] Continuation of Ser. No. 606,656, Aug. 21, 1975, abandoned.

[30] Foreign Application Priority Data

Aug. 26, 1974 [CH] Switzerland .................. 11582/74
Sep. 9, 1974 [CH] Switzerland .................. 12157/74
Jul. 9, 1975 [CH] Switzerland .................. 8963/75

[51] Int. Cl.³ .................. C07D 333/24; A61K 31/38
[52] U.S. Cl. .................. 549/64; 424/275
[58] Field of Search .................. 260/332.2 C, 329 S; 549/64

[56] References Cited
PUBLICATIONS
CIBA, "Chem. Abst.," vol. 47, p. 1399.
CIBA, "Chem. Abst.," vol. 60, p. 10847.

*Primary Examiner*—Alan Siegel

*Attorney, Agent, or Firm*—Jon S. Saxe; Bernard S. Leon; Frank P. Hoffman

[57] ABSTRACT

The invention relates to sulphothiophene-carboxylic acids of the following formula

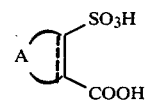

I wherein A together with the two carbon atoms to which it is attached forms the group

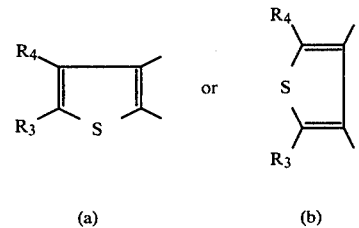

(a)          (b)

and the broken line represents the double bond present in group (a), $R_3$ and $R_4$ each represent a hydrogen atom or a lower alkyl group; and the halides and lower alkyl esters thereof.

3 Claims, No Drawings

THIOPHENE DERIVATIVES

This is a continuation of application Ser. No. 606,656, filed Aug. 21, 1975, now abandoned.

The present invention relates to thiophene derivatives. More particularly, the invention is concerned with sulphothiophene-carboxylic acids, halides and/or lower alkyl esters thereof.

The sulphothiophene-carboxylic acids provided by the present invention have the following general formula

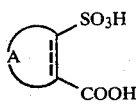   I wherein A together with the two carbon atoms to which it is attached forms the group

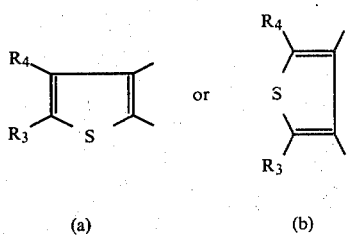

(a)        (b)

and the broken line represents the double bond present in group (a), $R_3$ and $R_4$ each represent a hydrogen atom or a lower alkyl group.

The halides and/or lower alkyl esters of the sulphothiophene-carboxylic acids of formula I have the following general formulae

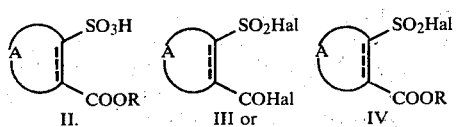

II.        III or        IV wherein A have the meaning indicated above, R represents a lower alkyl group and Hal represents a halogen atom.

As used in this description and in the accompanying claims, the term "lower alkyl" denotes a straight-chain or branched-chain saturated hydrocarbon group containing from 1 to 4 carbon atoms such as methyl, ethyl, propyl, isopropyl, tert.butyl and the like. The term "halogen" denotes chlorine, bromine, fluorine and iodine.

A preferred group of compounds of formulae I–IV comprise those in which $R_3$ and $R_4$ each represent a hydrogen atom.

According to the process provided by the present invention, the sulphothiophene-carboxylic acids, their halides and/or their lower alkyl esters are manufactured by the process which comprises:

(a) for the preparation of the acids, of formula I, converting a compound of the general formula

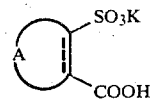   V wherein A has the meaning indicated above, into the corresponding free sulphonic acid, or (b) for the preparation of the lower alkyl ester of formula III, esterifying the free sulphonic acids of formula I, or (c) for the preparation of the halides of formula III, treating a compound of formula V above with a halogenating agent, or (d) for the preparation of the compounds of formula IV, treating a lower alkyl ester of formula II above with a halogenating agent or treating a halide of formula III above with a lower alkanol.

The conversion of a compound of formula V into the free acid of formula I is carried out in a manner known per se; for example, with a strong ion exchanger.

The esterification of an acid of formula I to give an ester of formula II is carried out autocatalytically (presence of the sulpho group) in an alcohol/chloroform mixture. For the formation of the methyl ester, the acid is dissolved in methanol/chloroform and the mixture obtained is heated to the boiling point of the ternary azeotrope (methanol/chloroform/reaction water).

The halogenation of a compound of formula V can be performed, for example, with 2 mols of phosphorus pentachloride and in the presence of phosphorus oxychloride as the solvent at a temperature between 30° C. and the boiling point of phosphorus oxychloride. However, in place of phosphorus oxychloride there can also be used an inert organic solvent (e.g. dioxane, chloroform, carbon tetrachloride, benzene, toluene and the like).

The esterification of a compound of formula III to give a corresponding ester of formula IV is carried out using an appropriate alcohol, especially methanol, at a temperature between room temperature and the reflux temperature of the mixture. As the solvent there can be used the alcohol or an inert solvent (e.g. chloroform, carbon tetrachloride, dioxane or benzene).

The starting materials of formula V can be prepared by conversion of a compound of the general formula

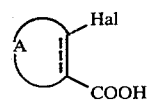   VI in the potassium salt of formula V.

The conversion of a halothiophene carboxylic acid of formula VI into a potassium salt of a sulphothiophene carboxylic acid of formula V is carried out according to methods known per se by reaction with sodium hydrogen sulphite in the presence of a copper (I) salt catalyst, especially copper (I) chloride, and reacting the product obtained with potassium chloride. The reaction with sodium hydrogen sulphide should be carried out at a temperature of 143° C. in order to obtain optimum yields.

Of the compounds of formula VI, 3-chloro-thiophene-2-carboxylic acid and 4-bromo-thiophene-3-carboxylic acid are known, the former having been prepared in a relatively complicated manner. A more facile method for the preparation of 3-chloro-thiophene-2-carboxylic acid consists in converting the known 3-hydroxy-thiophene-2-carboxylic acid methyl ester in an inert solvent boiling above 80° C. (e.g. chloroform or dioxane) with a chlorinating agent (e.g. phosphorus pentachloride) into 3-chloro-thiophene-2-carboxylic acid chloride and hydrolysing this acid chloride to the corresponding acid. In an analogous manner, there can also be prepared substituted 3-chloro-thiophene-2-carboxylic acids (compounds of formula VI in which Hal represents a chlorine atom and A together with the two carbon atoms to which it is attached forms the group

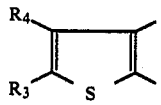

in which R₃ and/or R₄ represents other than a hydrogen atom). Although for the preparation of a compound of formula V there can, in principle, also be used a bromo compound (e.g. the known 4-bromo-thiophene-3-carboxylic acid) it is recommended to use the corresponding chloro compound. 4-Chlorothiophene-3-carboxylic acid, which has not been described in the literature, can be prepared from the known 3-keto-thiophene-4-carboxylic acid methyl ester by converting this ester by means of phosphorus pentachloride with aromatisation into 4-chloro-thiophene-3-carboxylic acid chloride and hydrolysing this acid chloride to the corresponding acid. In an analogous manner there can also be prepared substituted 4-chloro-thiophene-3-carboxylic acids (compounds of formula VI in which Hal represents a chlorine atom and A together with the two carbon atoms to which it is attached forms the group

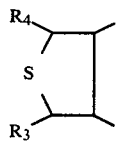

in which R₃ and/or R₄ represents other than a hydrogen atom).

The sulphothiophene-carboxylic acids, their halides and/or their lower alkyl ester are useful as intermediates for the preparation of thienothiazine derivatives having anti-inflammatory, analgesic and antirheumatic activity. These thienothiazine derivatives have the general formula

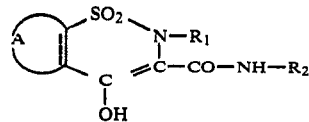

VII wherein A have the meaning indicated above, $R_1$ represents a lower alkyl group and $R_2$ represents the residue of an aromatic heterocyclic ring containing from 1 to 4 hetero atoms, which may be substituted by one or two lower alkyl groups, or a phenyl group which may be substituted by halogen, hydroxy, lower alkyl, trifluoromethyl or lower alkoxy.

The term "residue of an aromatic heterocyclic ring containing from 1 to 4 hetero atoms which may be substituted by one or two lower alkyl groups" includes residues of 5- or 6-membered aromatic heterocyclic rings containing 1–4 nitrogen and/or oxygen and/or sulphur atoms and which may be substituted by one or two lower alkyl groups such as 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 6-methyl-2-pyridyl, 1,2,3,4-tetrazol-5-yl and the like.

A preferred group of thienothiazine derivatives of formula VII comprises those in which $R_3$ and $R_4$ each represent a hydrogen atom. $R_1$ preferably represents the methyl group. $R_2$ preferably represents the 2-thiazolyl, 5-isoxazolyl or 2-pyridyl group.

An especially preferred thienothiazine derivative of formula VII is 4-hydroxy-2-methyl-N-(2-thiazolyl)-2H-thieno[2,3-e]-1,2-thiazine-3-carboxamide 1,1-dioxide.

The thienothiazine derivatives of formula VII can be prepared starting from the sulphothiophene-carboxylic acids, halides and/or lower alkyl ester thereof according to the following reaction scheme:

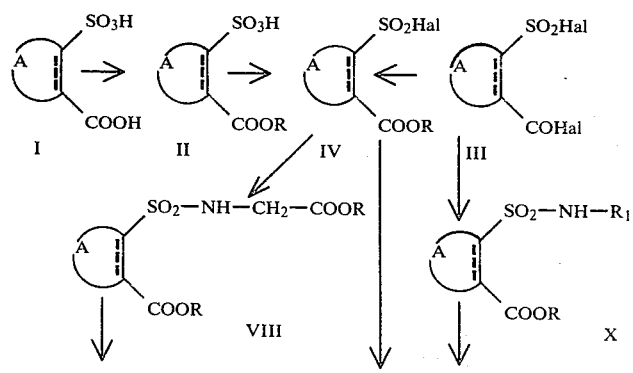

-continued

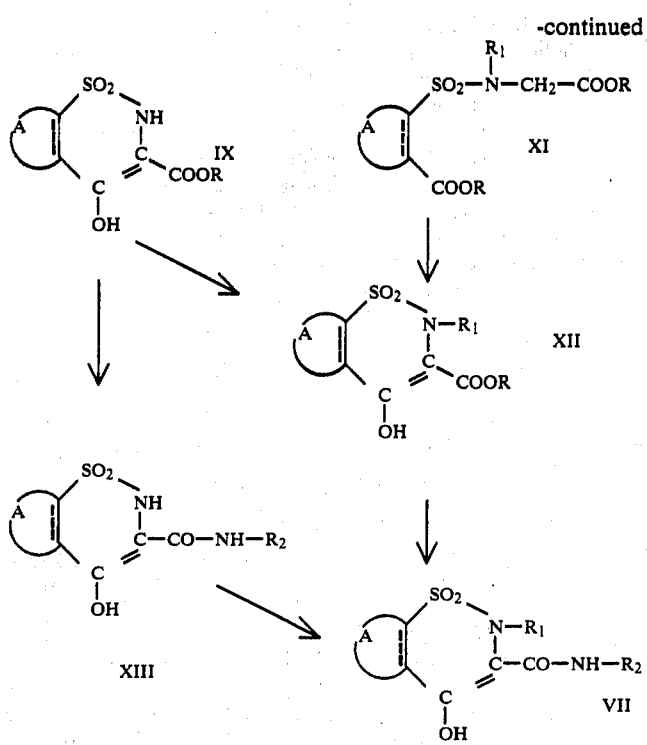

The following Examples illustrate the process provided by the present invention:

EXAMPLE 1

52.1 g of phosphorus pentachloride are dissolved in 600 ml of absolute carbon tetrachloride and heated to boiling, whereupon a solution of 15.8 g of 3-hydroxy-2-methoxycarbonylthiophene in 200 ml of carbon tetrachloride is added dropwise during 3 hours. The mixture is boiled to reflux for 13 hours, the carbon tetrachloride is distilled off and the mixture is evaporated almost to dryness in vacuo. 450 ml of water are added dropwise while cooling, whereupon the mixture is heated to boiling and then allowed to cool. The resulting precipitate is filtered off under suction and boiled up with 10 g of active carbon in a solution of 25 g of sodium bicarbonate. The active carbon is then filtered off under suction and the cooled solution is acidified with hydrochloric acid. There is obtained 3-chlorothiophene-2-carboxylic acid of melting point 185°–186° C.

In a glass autoclave, 8.6 g of 3-chlorothiophene-2-carboxylic acid are dissolved in 23 ml of water containing 2.1 g of sodium hydroxide, whereupon a solution of 5.6 g of sodium bisulphite in 16 ml of water is added and the solution made just alkaline with a 30% sodium hydroxide solution. The mixture is then treated with 0.43 g of copper (I) chloride and heated at 143° C. for 16 hours. After cooling, the red copper oxide is filtered off under suction. The filtrate is then acidified with 7 ml of concentrated hydrochloric acid, by which means the unreacted starting material precipitates out. The latter is removed by shaking out with methylene chloride. The acidic solution is treated with 12 g of potassium chloride while warming and, after cooling to 0° C., the potassium salt of 3-sulphothiophene-2-carboxylic acid separates as colourless crystals.

8.2 g of the potassium salt of 3-sulphothiophene-2-carboxylic acid are dissolved in 50 ml of water. This solution is passed through an ion-exchange column which is charged with protons, after which the column is rinsed with water until the solution flowing out has a pH value of 5. The solution is evaporated to dryness in vacuo and the crystalline residue is recrystallised from a small amount of water. There is obtained pure 3-sulphothiophene-2-carboxylic acid.

7.6 g of 3-sulphothiophene-2-carboxylic acid are dissolved in 140 ml of absolute methanol and 65 ml of absolute chloroform and boiled to reflux. The water of reaction is distilled off over a packed column (1 m) as a ternary azeotrope (chloroform, methanol, water). The mixture is evaporated in vacuo. To remove traces of methanol, the residue is treated with 100 ml of chloroform and the resulting mixture evaporated under atmospheric pressure. The remaining brown oil consists of 3-sulphothiophene-2-carboxylic acid methyl ester and crystallises immediately after cooling. However, the crystals are hygroscopic and deliquesce in the air.

7.4 g of crude 3-sulphothiophene-2-carboxylic acid methyl ester are dissolved in 50 ml of thionyl chloride and boiled to reflux for 16 hours. The mixture is then evaporated to dryness in vacuo and the remaining bright-yellow oil is brought to crystallisation with petroleum ether. There is obtained 3-chlorosulphonylthiophene-2-carboxylic acid methyl ester.

EXAMPLE 2

50 g (0.203 mol) of the monopotassium salt of 3-sulphothiophene-2-carboxylic acid are suspended in 250 ml of phosphorus oxychloride and while stirring there are added 85 g (0.406 mol) of phosphorus pentachloride [vigorous hydrogen chloride evolution]. The mixture is then heated on the water bath while stirring for a further 90 minutes and then cooled to room temperature. The inorganic salts are filtered off under suction and the phosphorus oxychloride distilled off in vacuo as well as possible. To remove inorganic salts still present, the oily residue is dissolved in 400 ml of dry chloroform, filtered and evaporated. The oily residue crystallises on cooling and consists of 3-chlorosulphonylthiophene-2-carboxylic acid chloride.

48 g (0.196 mol) of the obtained 3-chlorosulphonylthiophene-2-carboxylic acid chloride are dissolved in 500 ml of absolute chloroform, 9.6 g (0.3 mol) of absolute methanol are added and the mixture is heated to reflux for 3 hours [until no more hydrogen chloride evolution]. The mixture is evaporated to dryness in vacuo and the residue allowed to crystallise. There is obtained pure 3-chlorosulphonylthiophene-2-carboxylic acid methyl ester.

EXAMPLE 3

25 g of 3-keto-thiophene-4-carboxylic acid methyl ester dissolved in a small amount of absolute carbon tetrachloride are added dropwise during 2 hours to a boiling solution of 100 g of phosphorus pentachloride in 250 ml of absolute carbon tetrachloride. The mixture is then boiled to reflux for a further 15 hours until termination of the hydrogen chloride evolution and evaporated in vacuo, the bulk of the phosphorus chlorides being expelled. The residue is stirred with ice-water for 1 hour, whereupon the organic phase is separated and the aqueous phase shaken out once more with methylene chloride. The combined organic phases are dried over sodium sulphate and evaporated. The remaining brown oil consists of 4-chlorothiophene-3-carboxylic acid chloride. This oil is heated with a 2-N aqueous sodium hydroxide solution at 50° C. until a homogeneous brown solution results. The latter is shaken out once with methylene chloride and acidified with concentrated hydrochloric acid. The precipitated crystals are filtered off under suction and consist of crude 4-chlorothiophene-3-carboxylic acid. For purification, the crystals are dissolved in a sodium bicarbonate solution and re-precipitated with concentrated hydrochloric acid; melting point 164° C. (recrystallisation from water).

In a glass autoclave, 8.6 g of 4-chlorothiophene-3-carboxylic acid are dissolved in 23 ml of water containing 2.1 g of sodium hydroxide, whereupon a solution of 5.6 g of sodium bisulphite in 16 ml of water is added and the solution made just alkaline with a 30% sodium hydroxide solution. The solution is treated with 0.43 g of copper (I) chloride and heated at 143° C. for 16 hours. After cooling, the red copper oxide is filtered off under suction. The filtrate is acidified with 7 ml of concentrated hydrochloric acid and the unreacted starting material precipitates out, the latter being removed by shaking out with ether. The acidic solution is treated with 12 g of potassium chloride while warming and, after cooling to 0° C., the potassium salt of 4-sulphothiophene-3-carboxylic acid separates as colourless crystals. The crystals are dissolved in 50 ml of water and the solution passed through an ion-exchange column which is charged with protons, after which the column is rinsed with water until the solution flowing out has a pH value of 5. The eluate is evaporated to dryness in vacuo. There is obtained 4-sulphothiophene-3-carboxylic acid as a crystalline residue of melting point 154° C. (recrystallisation from water).

7.6 g of 4-sulphothiophene-3-carboxylic acid are dissolved in 140 ml of absolute methanol and 65 ml of absolute chloroform and boiled to reflux. The water of reaction is distilled off over a packed column (1 m) as a ternary azeotrope (chloroform, methanol, water). The mixture is evaporated in vacuo. To remove traces of methanol, the residue is treated with 100 ml of chloroform, whereupon the solution is evaporated at atmospheric pressure. The remaining brown oil crystallises immediately after cooling and consists of 4-sulphothiophene-3-carboxylic acid methyl ester [hygroscopic crystals which deliquesce in the air].

7.4 g of crude 4-sulphothiophene-3-carboxylic acid methyl ester are dissolved in 50 ml of thionyl chloride and boiled at reflux for 16 hours. The mixture is then evaporated to dryness in vacuo and the remaining bright-yellow oil is brought to crystallisation with petroleum ether. There is obtained 4-chlorosulphonylthiophene-3-carboxylic acid methyl ester of melting point 71° C. (recrystallisation from petroleum ether).

EXAMPLE 4

94.6 g (0.384 mol) of the monopotassium salt of 4-sulphothiophene-3-carboxylic acid are suspended in 390 ml of phosphorus oxychloride and while stirring there are added 160.8 g (0.768 mol) of phosphorus pentachloride [vigorous hydrogen chloride evolution]. The mixture is then heated on the water bath while stirring for 3 hours and cooled to room temperature. The inorganic salts are filtered off and the phosphorus oxychloride distilled off in vacuo as well as possible. To remove inorganic salts still present, the residue is dissolved in 400 ml of dry chloroform, filtered and evaporated. The residue crystallises on cooling and consists of 4-chlorosulphonylthiophene-3-carboxylic acid chloride.

Having now particularly described and ascertained the nature of our said invention and in what manner the same is to be performed, we declare that what we claim is:

1. Sulphothiophene-carboxylic acids of the general formulae

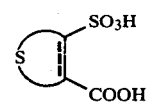
I

Wherein A together with the two carbon atoms to which it is attached forms the group

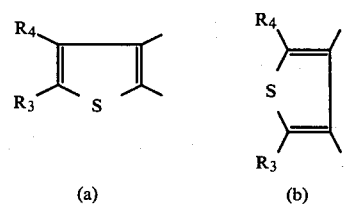

(a)        (b)

and the broken line represents the double bond present in group (a), $R_3$ and $R_4$ each represent a hydrogen atom or a lower alkyl group.

2. 3-Sulphothiophene-2-carboxylic acid.
3. 4-sulphothiophene-3-carboxylic acid.

* * * * *